United States Patent [19]

Sanders et al.

[11] Patent Number: 5,523,479
[45] Date of Patent: Jun. 4, 1996

[54] PROCESS FOR THE PREPARATION OF ETHERCARBOXYLIC ACIDS

[75] Inventors: Josef Sanders, Leverkusen; Klaus König, Odenthal, both of Germany

[73] Assignee: Bayer Aktiengesellschaft, Germany

[21] Appl. No.: 230,282

[22] Filed: Apr. 20, 1994

[30] Foreign Application Priority Data

May 4, 1993 [DE] Germany .................. 43 14 627.9

[51] Int. Cl.⁶ .................. C07C 59/10; C07C 59/125; C07C 59/245
[52] U.S. Cl. .................. 562/583; 560/180; 560/186; 560/187; 562/587; 562/588
[58] Field of Search .................. 562/583, 587, 562/588; 560/180, 186, 187

[56] References Cited

U.S. PATENT DOCUMENTS

| | | | |
|---|---|---|---|
| 4,948,915 | 8/1990 | Keen | 560/187 |
| 4,996,356 | 2/1991 | Takahashi et al. | 562/587 |
| 5,034,559 | 7/1991 | Hickmann | 560/180 |
| 5,081,285 | 1/1992 | Unruh et al. | 560/187 |

OTHER PUBLICATIONS

March, '*Advanced Organic Chemistry*', 3rd ed., John Wiley & Sons, New York (1985), pp. 351, 684–685.

*Primary Examiner*—José G. Dees
*Assistant Examiner*—Barbara S. Frazier
*Attorney, Agent, or Firm*—Joseph C. Gil; N. Denise Brown

[57] ABSTRACT

A process for the preparation of carboxylic acids which contain ether groups by the catalytically accelerated addition of alcoholic hydroxyl groups from mono- or polyhydric alcohols to tertiary-alkyl esters of $\alpha,\beta$-unsaturated carboxylic acids, and followed with acid hydrolysis of the tertiary-alkyl $\beta$-ethercarboxylate obtained as intermediates in this way.

4 Claims, No Drawings

PROCESS FOR THE PREPARATION OF ETHERCARBOXYLIC ACIDS

BACKGROUND OF THE INVENTION

The present invention relates to a novel process for the preparation of ethercarboxylic acids by 1) adding alcohols to tertiary-alkyl esters of α,β-unsaturated carboxylic acids to form the β-ethercarboxylate, followed by 2) acid hydrolysis of the β-ethercarboxylate to form the ethercarboxylic acid.

German 212,733 describes a process for the preparation of 3-alkoxypropionates by reacting methyl acrylate with lower monoalcohols in the presence of Ni acetoacetonate and butyllithium. European application 254,291 describes a process for the preparation of optionally substituted 3-alkoxypropionates by reacting monoalcohols or diols with optionally substituted acrylates in the presence of anionic ion exchangers which are present in the basic form. The European application 291,207 describes 3-alkoxypropionic acids, prepared by reacting aliphatic diols or alkoxylation products of aliphatic diols with acrylonitrile in DMF and subsequent hydrolysis of the 3-alkoxypropionitrile which is obtained.

Although the process products in the publications mentioned are intermediates for the preparation of β-ethercarboxylic acids, all these methods have the disadvantage that their commercial application is very difficult. Thus, in the German Application 212,733, the recommended catalysts are relatively expensive and, in addition, it is very difficult and complicated to remove them from the corresponding addition compounds. The process is also restricted to monoalcohols as starting materials. The process according to the European Application 254,291 is restricted to monoalcohols and diols. In addition, a large excess of the alcohol component, with respect to the α,β-unsaturated carboxylic acid, is required in order to produce an acceptable degree of conversion.

Similarly, the process in European Application 291,207 is restricted to the use of diols, along with the additional disadvantage that here dimethylformamide is required as the solvent and this can be removed from the addition product only with great difficulty. Also, hydrolysis of the intermediate product obtained can cause problems. If concentrated hydrochloric acid is used in excess, such as is described in European Application 291,207, then undesired ether decomposition reactions must be expected to take place during hydrolysis. However, if the hydrolysis is performed in the presence of strong bases such as sodium or potassium hydroxide, then at least equivalent amounts of bases are required, which produces correspondingly large amounts of salt when subsequently releasing the acids by neutralization, for example, with hydrochloric acid.

Incidentally, in all the methods in the prior art mentioned which use either methyl or ethyl (meth)acrylates, it is a common factor that undesired side reactions proceed via transesterification of the acrylate used, with the release of methanol or ethanol. The released methanol or ethanol can again add on to the acrylate used. Obviously, this amounts to a further undesired side reaction.

DESCRIPTION OF THE INVENTION

Surprisingly, it has now been found that β-ethercarboxylic acids can be prepared without the disadvantages described hereinabove. When mono- or polyhydric alcohols of the type mentioned in more detail hereinbelow are added to tertiary-alkyl esters of α,β-unsaturated carboxylic acids of the type mentioned by way of example hereinbelow, in the presence of catalysts of the type mentioned by way of example hereinbelow, and the ether carboxylates obtained in this way are hydrolyzed in the presence of dilute inorganic acids to form the corresponding β-ethercarboxylic acids. Side reactions of the type mentioned hereinabove are reduced by the use of the tertiary-alkyl esters of α,β-unsaturated carboxylic acids, and thus the yields and qualities of the end products are improved. Incidentally, removal of the tertiary-alkyl groups during the course of the hydrolysis reaction presents no real difficulty so that even here side reactions, such as e.g. ether decomposition, may be avoided.

More specifically, the present invention is directed to a process for the preparation of carboxylic acids which contain ether groups, and correspond to the general formula:

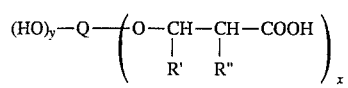

characterized in that, in a first process step, 1 mole of an alcohol of the formula $$Q(OH)_{x+y}$$

wherein:
Q represents a radical obtained by removing the hydroxyl groups from a (x+y)hydric alcohol having a molecular weight of from 32 to 6000,
R' and R" represent identical or different radicals being hydrogen or a methyl group, wherein at least one of the radicals is hydrogen,
x represents a number from 1 to 6, and
y represents a number from 0 to 5, wherein the sum x+y has a value from 1 to 6.

This process comprises the steps of
a) reacting
i) 1 mole of a polyhydric alcohol corresponding to the general formula $$Q(OH)_{x+y}$$

wherein:
Q represents a radical obtained by removing the hydroxyl groups from a (x+y)hydric alcohol with a molecular weight in the range 32 to 6000,
x represents a number from 1 to 6, and
y represents a number from 0 to 5, wherein the sum x+y has a value from 1 to 6; with
ii) at least x moles of tertiary-alkyl esters of, β-unsaturated carboxylic acids corresponding to the general formula:

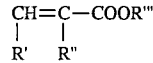

wherein
R' and R" represent identical or different radicals being hydrogen or a methyl group, wherein at least one of the radicals is hydrogen, and
R''' represents a tert.-alkyl radical,
and wherein:
x represents a number from 1 to 6; at temperatures of 0° to 100° C., in the presence of catalysts which accelerate the addition of alcoholic hydroxyl groups to the α,β-unsaturated carboxylic acid derivatives, thereby forming a tertiary-alkyl β-ethercarboxylates; and
b) hydrolyzing said tertiary-alkyl β-ethercarboxylates in the presence of acids to form the corresponding β-ethercarboxylic acids.

Suitable starting compounds for the process according to the invention include alcohols corresponding to the general formula:

$$Q(OH)_{x+y}$$

wherein:
Q represents a radical obtained by removing the hydroxyl groups from a (x+y)hydric alcohol with a molecular weight in the range 32 to 6000,
x represents a number from 1 to 6, and
y represents a number from 0 to 5, wherein the sum x+y has a value from 1 to 6.
Q preferably represents a radical which possesses an ether group, such as can be obtained, for example, by removing the hydroxyl groups from a polyetherdiol and -triol having a molecular weight in the range of 300 to 6000.

It is preferred that x represents a number from 1 to 3, and y represents a number from 0 to 2, wherein: the sum x+y is 2 or 3. Mixtures of polyetherdiols and -triols with the definition mentioned may obviously also be used as a starting material.

Some specific examples of suitable alcohols which correspond to the general formula:

$$Q(OH)_{x+y}$$

include, for example, methanol, ethanol, the isomeric propanols, butanols, pentanols, hexanols, higher fatty alcohols such as e.g. stearyl alcohol, ethylene glycol, the isomeric propylene glycols, dihydroxycyclohexanes, di(hydroxymethyl)cyclohexanes, glycerine, trimethylolpropane, sorbitol, saccharose, pentaerythritol and dipentaerythritol. Polyetherpolyols or mixtures of polyetherpolyols such as those that are obtained, for example, by the addition of propylene oxide and/or ethylene oxide to the alcohols specified hereinabove are particularly suitable, wherein the functionality of the starter molecules and the degree of alkoxylation correspond to the data given hereinabove with respect to the radical Q and the subscripts x and y.

Particularly preferred compounds are those polyetherpolyols of the disclosed formula which have a molecular weight of 300 to 4000 and an (average) hydroxyl functionality of 2 to 3. These are polyetherpolyols which are known per se from polyurethane chemistry, such as are described in, for example, European Application 380,993, the disclosure of which is herein incorporated by reference.

The tertiary-alkyl esters corresponding to the general formula:

$$\begin{array}{c} CH=C-COOR''' \\ |\quad\ | \\ R'\ \ R'' \end{array}$$

are preferably tertiary-butyl esters of acrylic acid, methacrylic acid, crotonic acid or isocrotonic acid Tertiary-butyl acrylate and tertiary-butyl methacrylate are particularly preferred.

Suitable catalysts for the addition reaction of alcohols to $\alpha,\beta$-unsaturated carboxylic acids include, for example, alkali metal organyls, such as, for example, butyl lithium or phenyllithium, Grignard compounds including, for example, ethyl magnesium bromide, ammonium, alkali metal and alkaline earth metal hydroxides, alkali metal and alkaline earth alcoholates and phenolates, amines such as, for example, triethylamine or pyridine, guanidine, phosphine, ion exchangers which are present in the OH-form, Ni acetylacetonate and dialkyl tin oxides. Sodium hydroxide, potassium hydroxide and potassium tertiary-butanolate are particularly preferred.

The starting materials are reacted in the presence of catalysts takes place in a manner which is known per se, in a solvent or preferably without a solvent, within the temperature range 0° to 100° C., preferably 20° to 80° C., until the hydroxyl value of the reaction product reaches the theoretical value or a constant value. At least x moles, and preferably at least 1.1×moles of the tertiary-alkyl ester of the unsaturated carboxylic acid are used per mole of alcohol that corresponds to the general formula:

$$Q(OH)_{x+y}$$

when performing the first step of the process according to the invention, wherein x has the meaning and preferred meaning mentioned hereinabove. Since the reaction of the tertiary-alkyl ester does not generally proceed quantitatively in the process according to the invention, it is also recommended that more than the stoichiometric amount (i.e. at least 1.1×moles per mole) of the tertiary-alkyl ester, with respect to the alcohol, be used when preparing process products which contain hydroxyl groups. If the unsaturated carboxylate is present in a subequivalent amount, with respect to the amount of hydroxyl groups contained in the alcohol component, specific products are obtained which still contain free hydroxyl groups that are available for further reactions. On the other hand, an excess of the carboxylate is advantageous or necessary for the complete conversion of the hydroxyl groups in the alcohols. This excess of carboxylate can be removed from the reaction mixture after completion of the reaction, for example, by distillation, and may then be used again.

The catalysts are generally used in an amount of 0.05 to 20 mol. %, preferably 1 to 10 mol. %, with respect to the total amount of hydroxyl equivalents present in the alcohol component used.

Suitable solvents for this reaction are those which are inert under the reaction conditions. Those which may be considered include, for example, diethyl ether, ethylene glycol dimethyl ether, tetrahydrofuran, dioxan, tert.-butanol, benzene, toluene, chlorobenzene, dimethylformamide, dimethylsulphoxide, N-methylpyrrolidone and acetonitrile. However, the reaction is preferably performed in the material itself, without a solvent.

Hydrolysis of the optionally substituted 3-alkoxy-propionic acid tertiary-alkyl ether carboxylates obtained as intermediates takes place by methods which are known per se including, for example, by reacting with dilute aqueous acids such as, for example, hydrohalic acids, sulfuric acid, phosphoric acid, sulfonic acids and halocarboxylic acids. A preferred acid is dilute hydrochloric acid at a concentration of 1 to 10 wt. %. For example, the reaction components may be stirred at a temperature of 20° to 100° C., preferably 60° to 100° C., until the acid value of a concentrated sample is constant. In some cases, it is advantageous to perform the hydrolysis in the presence of a solvent, which is then removed by distillation after the reaction has finished and which may then be used again. Solvents which may be used are those of the type mentioned above which are inert under the reaction conditions.

The ethercarboxylic acids prepared by the process according to the invention are characterized by low viscosities and low degrees of discoloration. They are suitable for preparing, for example, polyesters, polyetheramides, polyethercarbonates and the like. They may also be used either as they are, or in the form of their salts as emulsifiers or as catalysts. It is most preferred that the ethercarboxylic acids produced according to the invention are used in the form of their sodium or alkali metal salts as catalysts which can be built in during the preparation of polyurethane foams.

The examples described hereinbelow further illustrate details for the process of this invention. The invention, which is set forth in the foregoing disclosure, is not to be limited either in spirit of scope by these examples, Those skilled in the art will readily understand that known variations of the conditions of the following procedures can be used. Unless otherwise noted, all temperatures are degrees Celsius and all parts are parts by weight and all percentages are percentages by weight.

EXAMPLES

Example 1 a) Acrylate Addition 28.7 g (0.51 mol) of powdered potassium hydroxide are dissolved or dispersed, with vigorous stirring and warming to 40° C., in 2433 g (23.85 OH equivalents) of a polyethertriol with an OH value of 550, prepared by propoxylation of trimethylolpropane. Then, at this temperature, 1067 g (8.34 mol) of tertiary-butyl acrylate are added dropwise and regularly over the course of 5 hours, and stirring is then continued for an additional 16 hours at 40° C. After the dropwise addition of 50.5 g (0.51 mol) of 37% strength hydrochloric acid, the volatile constituents (73 g, mainly unconverted acrylate with a little tertiary-butanol) are distilled off under a water jet vacuum until the temperature of the liquid reaches 80° C. After filtration, a clear, slightly yellowish product is obtained with an acid value of 13.9 and an OH value of 267.6 mg KOH. This corresponds to 31.9% conversion of the hydroxyl groups initially present. An ester equivalent weight of 447.9 is calculated from this data.

b) Hydrolysis

A mixture of 3400 g (7.59 COOR equivalents) of the product from Example 1a), 3400 ml of water and 149.8 g (1.52 mol) of 37% strength hydrochloric acid is stirred at 95° C. until the distillation of tertiary-butanol comes to a standstill (ca. 8 h). The stirrer is switched off, the mixture is allowed to stand for 30 minutes, and the (upper) dilute acid phase is separated from the (lower) product phase. Then the remaining residual water is removed from the crude product by distillation under a 0.5 mbar vacuum until the temperature of the liquid is 60° C. A clear, yellowish product with an acid value of 104 is obtained.

Comparison Example to Example 1a)

Acrylate Addition 1149 g (11.26 OH equivalents) of the same polyethertriol used in Example 1a), 339 g (3.94 mol) of methyl acrylate, 12.5 g (0.22 mol) of powdered potassium hydroxide and 22 g (0.22 mol) of 37% strength hydrochloric acid are reacted according to the same procedure as described in Example 1a). Distillate: 158.6 g (mainly approximately equal amounts of acrylate and methanol). A turbid, yellowish product having an acid value of 9 and an OH value of 329.4 is obtained. This corresponds to 27.7% conversion of the hydroxyl groups initially present. An ester equivalent weight of 468.7 is calculated from this data.

Example 2 a) Acrylate Addition 1795 g (17.60 OH equivalents) of the same polyethertriol used in Example 1a), 1705 g (13.32 mol) of tertiary-butyl acrylate, 20.9 g (0.37 mol) of powdered potassium hydroxide and 36.8 g (0.37 mol) of 37% strength hydrochloric acid are reacted according to the same procedure as described in Example 1a). Distillate: 175 g (mainly acrylate with a little tertiary-butanol). A clear, slightly yellowish product with an acid value of 10.7 and an OH value of 114.1 is obtained. This corresponds to 62.9% conversion of the hydroxyl groups initially present. An ester equivalent weight of 290.2 is calculated from this data.

b) Hydrolysis 1555 g (5.36 COOR equivalents) of the product from Example 2a), 1555 g of water and 105.7 g (1.07 mol) of 37% strength hydrochloric acid are reacted following the same procedure as described in example 1b). A clear yellowish product with an acid value of 184.9 is obtained.

Comparison Example to Example 2a)

Acrylate Addition 913 g (8.95 OH equivalents) of the same polyethertriol used as described in Example 1a), 577 g (6.71 mol) of methyl acrylate, 10 g (0.18 mol) of powdered potassium hydroxide and 17,6 g (0.18 mol) of 37% strength hydrochloric acid are reacted following the same procedure as that described in Example 2a). Distillate: 241 g (mainly methyl acrylate and methanol). A turbid, yellowish product with an acid value of 10.1 and an OH value of 330.4 is obtained. This corresponds to 26.5 conversion of the hydroxyl groups initially present. An ester equivalent weight of 470.9 is calculated from this data.

In comparison examples to Examples 1a) and 2a), which are not in accordance with the invention, equimolar amounts of methyl acrylate are used each time instead of tertiary-butyl acrylate. The conversions obtained are clearly lower than the corresponding conversions produced with tertiary-butyl acrylate. In the case of methyl acrylate, the distillates contain considerable fractions of methanol, which points to the saponification of methyl acrylate by the basic catalyst. This is confirmed by the rate of conversion in comparison example 2, which is no higher than the rate of conversion in comparison example 1, despite the much higher amount of methyl acrylate used therein. Obviously, the catalyst was consumed here, which was why the reaction came to a standstill after only a low degree of conversion.

Example 3 a) Acrylate Addition 295 g (1 OH equivalent) of polyethertriol with an OH value of 190, prepared by ethoxylation of propylene glycol, 128 g (1 mol) of tertiary-butyl acrylate, 0.6 g (0.01 mol) of powdered potassium hydroxide and 1.1 g (0.01 mol) of 37% strength hydrochloric acid are reacted according to the same procedure as that described in Example 1a). Distillate: 24 g (mainly acrylate with a little tertiary-butanol). A clear, pale yellowish product with an OH value of 21.2 is obtained. This corresponds to 84.8% conversion of the hydroxyl groups initially present. An ester equivalent of 476.1 is calculated from this data.

b) Hydrolysis 160 g (0.34 COOR equivalents) of the product from Example 3a), 45 g of water and 16.6 g (0.16 mol) of 37% strength hydrochloric acid are reacted following the same procedure as described in example 1b). A clear, almost colorless product with an acid value of 142 is obtained.

Example 4 a) Acrylate Addition 1043 g (4.66 OH equivalents) of polyethedriol with an OH value of 250, prepared by propoxylation of 3-trimethylolpropane and subsequent ethoxylation of the propoxylated product (ratio PO:EO=1.1:98.9, by weight), 452 g (3.53 mol) of tert-butyl acrylate, 5.2 g (0.09 mol) of powdered potassium hydroxide and 9.2 g (0.09 mol) of 37oo strength hydrochloric acid were reacted following the same procedure as that described in Example 1a). Distillate: 97 g (mainly acrylate and a little tert.-butanol). A clear, pale yellowish product with an OH value of 57.7 is obtained. This corresponds to 66% conversion of the hydroxyl groups initially present. An ester equivalent weight of 467.6 is calculated from this data.

b) Hydrolysis 150 g (0.32 COOR equivalents) of product from Example 4a), 136.5 g of water and 13.5 g (0.14 mol) of 37% strength hydrochloric acid are reacted according to the same procedure as that described in Example 1b). A clear, pale yellowish product with an acid value of 114 is obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of carboxylic acids which contain ether groups and correspond to the general formula:

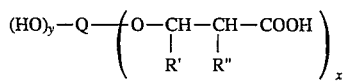

wherein:

Q represents a radical obtained by removing the hydroxyl groups from a (x+y)hydric alcohol having a molecular weight of from 32 to 6000, R' and R" represent identical or different radicals being hydrogen or a methyl group, wherein at least one of the radicals is hydrogen, x represents a number from 1 to 6, and y represents a number from 0 to 5, wherein the sum x+y has a value from 1 to 6;

comprising the steps of a) reacting i) 1 mole of a polyhydric alcohol corresponding to the general formula

wherein:

Q represents a radical obtained by removing the hydroxyl groups from a (x+y)hydric alcohol with a molecular weight in the range of 32 to 6000, x represents a number from 1 to 6, and y represents a number from 0 to 5, wherein the sum x+y has a value from 1 to 6; with ii) at least x moles of tertiary -alkyl esters of α,β-unsaturated carboxylic acids corresponding to the general formula:

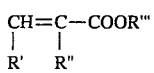

wherein

R' and R" represent identical or different radicals hydrogen or a methyl group, wherein at least one of the radicals is hydrogen, and R'" represents a tert.-alkyl radical, and wherein:

x represents a number of from 1 to 6;

at temperatures of 0° to 100° C., in the presence of catalysts which accelerate the addition of alcoholic hydroxyl groups to the α,β-unsaturated carboxylic acid derivatives, thereby forming tertiary-alkyl β-ethercarboxylates; and b) hydrolyzing said tertiary-alkyl β-ethercarboxylates in the presence of acids to form the corresponding β-ethercarboxylic acids.

2. The process of claim 1 wherein said tertiary-alkyl ester of the α,β-unsaturated carboxylic acid is selected from the group consisting of tertiary-butyl acrylate and tertiary-butyl methacrylate.

3. The process of claim 1 wherein said polyhydric alcohol is selected from the group consisting of i) polyetherdiols having a molecular weight of from 300 to 6000, ii) polyethertriols having a molecular weight of from 300 to 6000, and iii) mixtures thereof.

4. The process of claim 1 wherein said catalysts used in the addition reaction between said polyhydric alcohols and said α,β-unsaturated carboxylic acids are selected from the group consisting of sodium hydroxide, potassium hydroxide, and potassium tertiary-butanolate.

* * * * *